(12) United States Patent
Jin et al.

(10) Patent No.: US 11,717,503 B2
(45) Date of Patent: Aug. 8, 2023

(54) APPLICATION OF VALINE IN PREPARING MEDICINE FOR TREATING OR PREVENTING AVIAN INFLUENZA VIRUS INFECTION

(71) Applicant: Huazhong Agricultural University, Hubei (CN)

(72) Inventors: Meilin Jin, Hubei (CN); Qiang Zhang, Hubei (CN); Xiaotong Hu, Hubei (CN); Li Yang, Hubei (CN); Ting Wang, Hubei (CN); Xiaomei Sun, Hubei (CN); Chao Kang, Hubei (CN); Ming Zhong, Hubei (CN)

(73) Assignee: Huazhong Agricultural University, Hubei (CN)

( * ) Notice: Subject to any disclaimer, the term of this patent is extended or adjusted under 35 U.S.C. 154(b) by 87 days.

(21) Appl. No.: 17/146,413

(22) Filed: Jan. 11, 2021

(65) Prior Publication Data

US 2021/0220311 A1 Jul. 22, 2021

(30) Foreign Application Priority Data

Jan. 16, 2020 (CN) .......................... 202010048679.7

(51) Int. Cl.
*A61K 31/198* (2006.01)
*A61P 31/16* (2006.01)

(52) U.S. Cl.
CPC ............ *A61K 31/198* (2013.01); *A61P 31/16* (2018.01)

(58) Field of Classification Search
CPC .............................. A61K 31/198; A61P 31/16
See application file for complete search history.

(56) References Cited

U.S. PATENT DOCUMENTS

2004/0022827 A1* 2/2004 Satomi .................. A23L 33/175
514/561

OTHER PUBLICATIONS

Ospina-Rojas et al. "Leucine and valine supplementation of low-protein diets for broiler chickens from 21 to 42 days of age," Poultry Science, 2017. vol. 96, pp. 914-922 (Year: 2017).*
Chen et al. "Exogenous L-valine promotes phagocytosis to kill multidrug resistant bacterial pathogens," Frontiers in Immunology, 2017, vol. 8, article 207 (Year: 2017).*
Kakazu et al. "Extracellular Branched-chain amino acids, especially valine, regulate maturation and function of monocyte-derived dendritic cells," J. Immunol. 2007, vol. 179, pp. 7137-7146 (Year: 2007).*
Hashimoto et al. " Evidence for phagocytosis of influenza virus-infected, apoptotic cells by neutrophils and macrophage in mice," J. Immunology, 2007, vol. 178, pp. 2448-2457 (Year: 2007).*
Ashley L. Steed et al., "The microbial metabolite desaminotyrosine protects from influenza through type I interferon," Science 357, 498-502, pp. 1-5 (Aug. 4, 2017).

(Continued)

*Primary Examiner* — Shengjun Wang
(74) *Attorney, Agent, or Firm* — Mei & Mark LLP; Manni Li

(57) ABSTRACT

Application of valine in the preparation of a medicine for treating or preventing avian influenza virus infection. In a lethal mouse influenza infection model, the use of valine to treat infected mice can effectively improve the weight loss of mice, increase the survival rate of mice, and can effectively reduce the virus titer in the supernatant of the lung tissue of the infected mice.

3 Claims, 3 Drawing Sheets

(56) References Cited

OTHER PUBLICATIONS

C. Patrick Burns, "Isoleucine Metabolism by Leukemic and Normal Human Leukocytes in Relation to Cell Maturity and Type," Blood, vol. 45, No. 5, pp. 643-651 (May 1975).

C. Chen et al., "The Effect of Dietary Lysine Deficiency on the Immune Response to Newcastle Disease Vaccination in Chickens," Avian Diseases, 47(4), pp. 1346-1351 (2003).

Jian-Bo Luo et al., "The impaired intestinal mucosal immune system by valine deficiency for young grass carp (*Ctenopharyngodon idella*) is associated with decreasing immune status and regulating tight junction proteins transcript abundance in the intestine," Fish & Shellfish Immunology xxx, pp. 1-11 (2014).

M. M. M. Azzam et al., "Effect of excess dietary L-valine on laying hen performance, egg quality, serum free amino acids, immune function and antioxidant enzyme activity," British Poultry Science, pp. 1-23, DOI: 10.1080/00071668.2014.989487 (2014).

Xiangbing Mao et al., "L-Isoleucine Administration Alleviates Rotavirus Infection and Immune Response in the Weaned Piglet Model," Frontiers in Immunology, vol. 9, Article 1654, pp. 1-12, DOI: 10.3389/fimmu.2018.01654 (Jul. 16, 2018).

Zhang, Jie, et al., "Synthesis and Antitumor Activities of Rhein-Valine Adducts," Chemical Journal of Chinese Universities, vol. 37, No. 12, pp. 2159-2167 DOI: 10.7503/cjcu20160568 (Dec. 2016).

Li, Xiaoyue, et al., "Advance in the Research on ε-Poly-L-lysine and Its Antimicrobial Mechanisms," Crop Research, vol. 33, No. 6, pp. 608-614, DOI: 10.16848/j.cnki.issn.1001-5280.2019.06.25 (Sep. 2019).

Niu, Xiaotian, et al., "Effects of dietary Lysine Level on Growth, Feed Utilization, Serum Biochemical Indexes, Lysine Metabolizing Enzyme Activity and Related Gene Expression of *Leuciscus brandti*," Journal of Fisheries of China, vol. 43, No. 10, pp. 2154-2165, DOI: 10.11964/jfc.20190911963 (Oct. 2019).

Wang, Yubo, et al., "Effects of Valine Level in Low Protein Diets on Growth Performance, Carcass Traits and Meat Quality of Finishing Pigs," Acta Veterinaria et Zootechnica Sinica, 50(9), pp. 1832-1840, DOI: 10.11843/j. issn.0366-6964.2019.09.010 (2019).

Chen, Jiang, et al., "Effect of Valine Supplementation in Low-Protein Diets on Growth Performance, Slaughter Performance and Serum Indices of Broilers," Chinese Journal of Animal Nutrition, 31(4), pp. 1604-1612, DOI: 10.3969/j.issn.1006-267x.2019.04.017 (2019).

Huang, Hong-Ying, et al., "Effects of Valine and Isoleucine on Production Performance of Lactating Sows and Litters," Chinese Journal of Animal Nutrition, 20(3), pp. 281-287 (2008).

Zhang, Yongsheng, et al., "The research progress of valine in weaned pigs," Heilongjiang Animal Science and Veterinary Medicine, (01), pp. 46-49, DOI: 10.13881/j.cnki.hljxmsy.2018.05.0003 (2019).

Ren, Man, et al., "Beneficiary effects of isoleucine on antimicrobial pathogen infection on intestinal epithelial cells in weaned piglets," Abstract for meeting presentation (2014).

\* cited by examiner

APPLICATION OF VALINE IN PREPARING MEDICINE FOR TREATING OR PREVENTING AVIAN INFLUENZA VIRUS INFECTION

CROSS-REFERENCE TO RELATED APPLICATIONS

The subject application claims priority on Chinese Application No. CN202010048679.7 filed on Jan. 16, 2020 in China. The contents and subject matter of the Chinese priority application is incorporated herein by reference.

BACKGROUND OF THE INVENTION

Technical Field

The invention belongs to the technical field of biomedicine, and particularly relates to an application of valine in the preparation of a medicine for treating or preventing avian influenza virus infection.

Description of Related Art

The influenza virus belongs to the Orthomyxoviridae Influenza virus genus, and is a highly contagious infectious disease worldwide, and viruses that threaten human health continue to appear repeatedly. Worldwide, the annual influenza outbreak infects approximately 1 billion people, causing three to five million serious illnesses and up to one million deaths. Avian influenza virus belongs to the Orthomyxoviridae Influenza A virus genus. The disease mainly occurs in poultry and wild birds, seriously hindering the development of the poultry industry. Moreover, some of its subtypes (H5, H7, H9, H10) can also transmit to people cross-species, causing fever, cough, muscle aches, conjunctivitis, respiratory diseases and other symptoms, and even death in severe cases, posing a serious threat to human health.

The avian influenza virus has always been relatively mild and only spreads among animals. However, human cases of H7N9 influenza were first detected in Shanghai and Anhui in March 2013, proving that this virus is able to spread from poultry to humans across species isolation. Poultry hosts infected with H7N9 include chickens, ducks, geese, and quails, and wild hosts include waterfowls around rivers, lakes, and seas, as well as various migratory wild birds. Close contact with infected poultry, its secretions and excrement, or the virus-contaminated environment can cause human infection with H7N9 avian influenza virus. According to statistics from the World Health Organization (WHO), as of March 2018, the number of people infected with H7N9 worldwide has reached 1,564. Among them, a total of 1,438 cases and 570 deaths have been reported in China, with a fatality rate high up to 39.63%. Therefore, good prevention and control of avian influenza H7N9 can not only promote the healthy development of the livestock and poultry breeding industry, but also effectively maintain social and economic stability and ensure public health safety.

In the process of livestock and poultry breeding, the prevention and control technologies for avian influenza at home and abroad mainly include: culling, disinfection, biological safety, and vaccination. Although culling infected livestock and poultry can curb the spread of avian influenza to a certain extent, wild birds, as another important host of avian influenza, are difficult to control through culling. Moreover, large-scale culling of livestock and poultry will also cause huge economic losses. Another effective measure to prevent the occurrence of avian influenza is vaccination. When the vaccine used is the same as the clinically epidemic strain, the ideal protective effect can be obtained, but when the vaccine used is different from the epidemic strain, it cannot provide effective immune protection. There are many serotypes of the avian influenza virus, and the mixed infection of influenza viruses of different subtypes often occur genetic recombination to form new avian influenza viruses, which brings great difficulties to the development and application of vaccines. Immunization failures caused when vaccines used are different from epidemic strains often occur in production practice.

At present, the prevention of influenza virus infection is mainly vaccination. The treatment drugs mainly use some neuraminidase inhibitors and ion channel M2 protein inhibitors. However, the effectiveness of these drugs is limited and drug resistance may occur. Extensive antiviral resistance limits the clinical application of these inhibitors in the prevention and treatment of influenza infection. Moreover, clinical and experimental evidence also shows that prevention and treatment of influenza virus infection not only need to block the spread of the virus, but also need to reduce the inflammatory response of the virus infection to the host and damage to the lung epithelium, and protect epithelial cells from unnecessary cell death. Therefore, in the process of preventing avian influenza, in addition to strengthening the development of drugs such as vaccines and inhibitors, other biological preparations with highly effective anti-flu effects should also be actively developed.

As one of the three branched chain amino acids, valine is an essential amino acid that cannot be synthesized in the animal body but must be obtained from food protein. It has physiological functions such as carrying out oxidizing energy supply, promoting protein synthesis, and promoting gluconeogenesis, and plays an important role in the regulation of material metabolism and information transmission in the living body. Therefore, valine is widely used in nutritional additives, feed additives, flavoring agents, medicines, pesticides, health products, etc. Valine was separated from the pancreas extract by Von Group Besanez in 1856. It was not until 1906 that Fisher analyzed its chemical structure as α-aminoisovaleric acid. Zhang Yongsheng et al. (2019) reported that valine could increase the survival rate of weaned piglets, promote the growth and development of weaned piglets, and improve intestinal immune function. Zhang Jie et al. (2016) reported that the rhein-valine adduct has anti-tumor activity. Huang Hongying et al., (2008) reported that adding valine and isoleucine to sow diets could increase the daily feed intake and milk quality of lactating sows, and improve the growth performance of lactating piglets. Chen Jiang et al. (2019) reported that supplementing valine in low-protein diets could improve the growth performance and antioxidant capacity of broiler chickens. Wang Yubo et al., (2019) reported that low-valine diets reduced the average daily gain, hot carcass weight, scissors force and marbling scores of fattening pigs, increased muscle fat content, and caused a negative impact on growth performance, carcass traits, and water-holding capability, and high-valine diets did not further improve growth performance, but improved carcass traits and meat quality while enhancing insulin sensitivity. C. Chen et al., (2003) found that feeding lysine-deficient diets could lead to reduced antibody response after broiler chickens are vaccinated against Newcastle disease (NDV). According to skin basophil hypersensitivity monitoring, lysine deficiency also reduced cell-mediated immune function. Luo Jian-Bo et al., (2014) found that it affected the growth and intestinal immune status of grass carp. M. M. M. Azzam et al., (2014) reported that valine supplementation could increase the serum albumin concentration of laying hens. Ashley L. Steed et al., (2017) found that a microbial-related metabolite, desaminotyrosine (DAT), protected influenza by increasing type I interferon signaling and reducing lung immunopathology. This study shows that specific components of the gut microbiota have a distal effect by modulating the response of type I interferons to lethal infections.

Isoleucine is also one of the three branched-chain amino acids. It was first isolated from beet syrup in 1904 by Ehrlich, and later prepared from the trypsin hydrolysate of various proteins. It is found that although its chemical composition is the same as leucine, but its physical and chemical properties are different, it is confirmed as another amino acid, named isoleucine. Isoleucine is essential to certain physiological functions of animals. In humans and animals, isoleucine plays a vital role in immune function, including maintaining the development of immune organs and cells and stimulating the secretion of immune molecular substances. Isoleucine can also improve the health of cells and animals under certain challenging conditions. Burns C P (1975) has demonstrated that isoleucine can be specifically bound to immune cell proteins, such as lymphocytes, eosinophils and neutrophils. Mao Xiangbing et al., (2018) reported that adding isoleucine to the diet could improve the growth performance, immune function and antioxidant capacity of hosts. Ren Man et al., (2014) reported that isoleucine was beneficial to porcine intestinal epithelial cells to resist infection by pathogenic microorganisms. Isoleucine treatment of intestinal epithelial cells for 24 hours could significantly reduce the growth of *Salmonella* and *E. coli* in co-culture.

Lysine is a basic amino acid and is widely used in animal feed. It has the functions of promoting the growth and development of the body and improving immunity. Niu Xiaotian et al., (2019) reported that the lysine level in the feed caused a significant impact on the growth, feed utilization and blood biochemical indicators of Yaluo fish. Li Xiaoyue et al., (2019) reported that ε-poly-L-lysine could be used as a food preservative to extend the shelf life of food.

At present, most of the research on valine, lysine and isoleucine is currently based on nutrition and immunity improvement, and there are few reports on the antiviral research of these amino acids.

BRIEF SUMMARY OF THE INVENTION

The invention is directed to the difficulty about prevention and treatment of influenza virus infection, and intended to provide the application of valine in the preparation of a medicine for treating or preventing avian influenza virus infection. In order to achieve the above objectives, the invention adopts the following technical measures:

The application of valine in the preparation of a medicine for treating or preventing avian influenza virus infection, including the use of valine as the sole active ingredient or one of active ingredients for the preparation of a medicine for treating or preventing diseases with avian influenza virus infection.

In the above-mentioned application, preferably, the valine is used to prepare an interferon stimulant for the body infected with the avian influenza virus.

The avian influenza virus described above is preferably H7N9.

The above-mentioned medication is taken orally.

The symptoms of the infection described above include weight loss, death, and the proliferation of H7N9 influenza virus in the lungs due to H7N9 infection.

Compared with the prior art, the present invention has the following advantages:

(1) The valine of the invention can regulate the immune response of the host body, increase the body's elimination of the virus, and also reduce the inflammatory injury caused by overexpression of cytokines.

(2) The valine of the invention can improve the ability of the body to produce interferon and clear the virus in time after the animal body is infected with avian influenza virus.

(3) The valine of the invention can significantly inhibit the proliferation of H7N9 influenza virus in mice, improve the weight loss caused by H7N9 infection, and improve the survival rate of infected mice. Therefore, the valine has obvious resistance to H7N9 influenza virus infection.

BRIEF DESCRIPTION OF THE SEVERAL VIEWS OF THE DRAWINGS

FIG. 4A shows the effect on TNF-α (pg/mL); FIG. 4B shows the effect on IL-1β (pg/mL); FIG. 4C shows the effect on IFN-β (pg/mL); FIG. 4D shows the effect on IFN-γ (pg/mL).

DETAILED DESCRIPTION OF THE INVENTION

The experimental methods and conditions in the following examples are conventional methods unless otherwise specified. These examples are only used to illustrate the invention, and the protection scope of the invention is not limited by these examples. The technical solutions of the invention, unless otherwise specified, are conventional solutions in the field; unless otherwise specified, the reagents or materials are all sourced from commercial channels. The invention takes avian influenza virus H7N9 as an example to illustrate the application of valine in the preparation of a medicine for preventing or treating avian influenza virus infection. Since valine can significantly increase the interferon level of the body infected with avian influenza virus, it thus can also be used for other types of avian influenza virus infections.

Example 1

The effect of valine, isoleucine, and lysine on the body weight of mice infected with avian influenza virus:

The test animals were 8-week-old female C57BL/6 SPF (Specific-Pathogen-Free) mice, in a total of 40, randomly divided into 4 groups, 10 in each group, and all the animals were raised in an ABSL3 (Animal Biological Safety Level-3) laboratory.

The first group was a germ-free PBS control group taking intragastric administration; the second group was a group of mice taking intragastric administration of a valine solution; the third group was a group of mice taking intragastric administration of a isoleucine solution; and the fourth group was a group of mice taking a lysine solution.

The mice were given PBS, valine, isoleucine, and lysine solutions every day. One week later, all mice were nasally infected with 500 $EID_{50}$ H7N9 avian influenza viruses. After challenge, they were given the PBS, valine, isoleucine, and lysine solutions another 3 days. The mice were observed and weighed for 15 consecutive days, and the survival status was recorded.

Amino acid solutions: valine, isoleucine, and lysine were each formulated into a 500 mg/ml aqueous solution, and the daily dose for mice was 100 mg/mouse.

Figure 1:
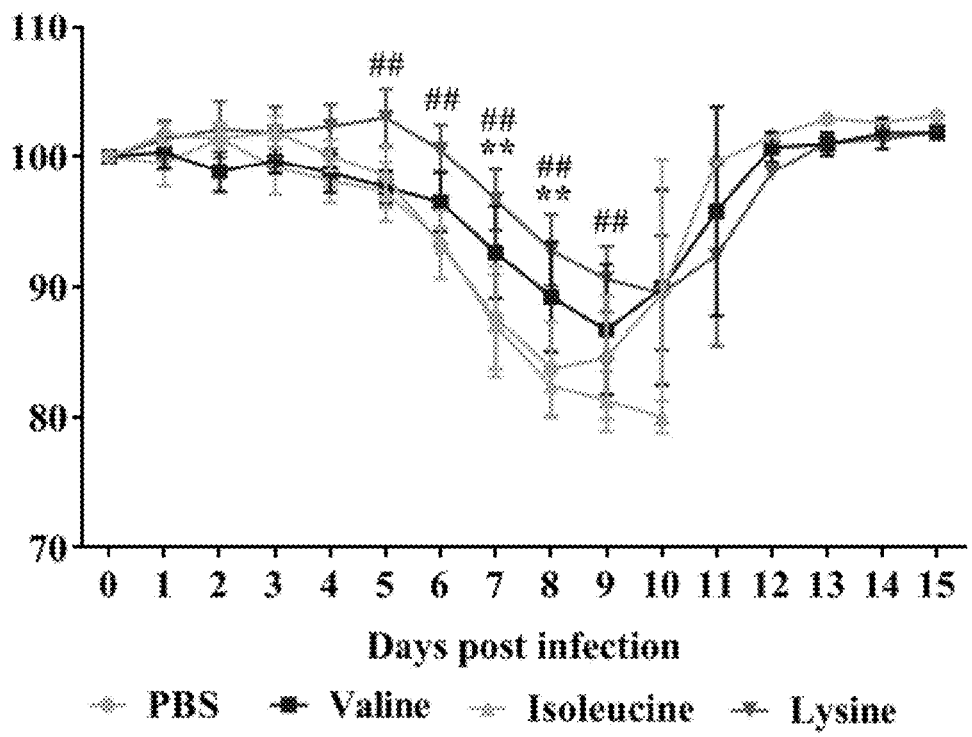
FIG. 1 is a schematic diagram showing the effect of oral administration of different amino acid solutions on the body weight of mice infected with H7N9 avian influenza virus, where the vertical axis shows the percentage over the initial body weight.
Figure 2:
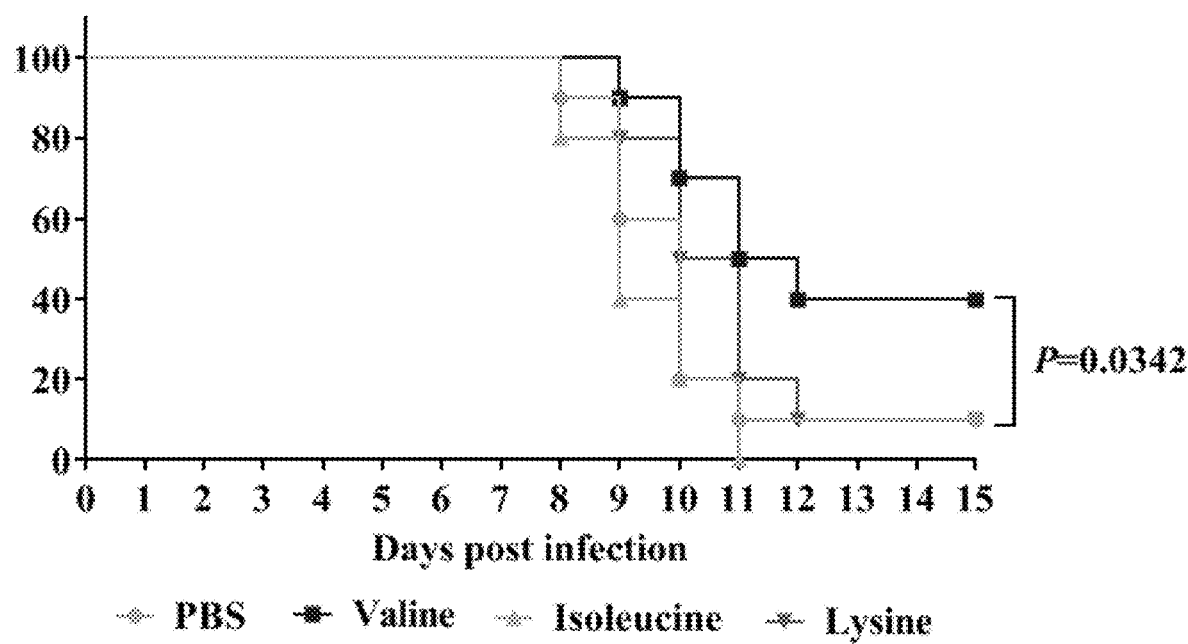
FIG. 2 is a schematic diagram showing the effect of oral administration of different amino acid solutions on the survival rate of mice infected with H7N9 avian influenza virus, where the vertical axis shows the survival rate.

1. Effect of Oral Administration of Amino Acid Solutions on the Body Weight of Mice Infected with H7N9 Avian Influenza Virus According to the results, in terms of body weight, oral administration of valine or lysine alleviated the weight loss of mice caused by H7N9 influenza virus infection, and especially in the 5-9 days after infection, the improvement effect was most obvious; but oral administration of isoleucine did not improve the weight loss. Instead, all mice died on the 10th day after infection (Table 1, FIG. 1).

oral administration of isoleucine died on the 11th day after influenza virus infection (Table 2, FIG. 2).

TABLE 2

Effect of oral administration of amino acid solutions on the survival rate of mice infected with H7N9 avian influenza virus

| Group | PBS control group | Valine group | Isoleucine group | Lysine group |
| --- | --- | --- | --- | --- |
| Number at the time of infection | 10 | 10 | 10 | 10 |
| Number of survivals 15 days post infection | 1 | 4 | 0 | 1 |
| Survival rate (%) | 10 | 40 | 0 | 10 |
| Mortality (%) | 90 | 60 | 100 | 90 |

Example 2

Application of valine in the preparation of a medicine for treating or preventing avian influenza virus infection The test animals were 8-week-old female C57BL/6 SPF (Specific-Pathogen-Free) mice, in a total of 20, randomly divided into 2 groups, 10 in each group, and all the animals were raised in an ABSL3 (Animal Biological Safety Level-3) laboratory. The first group was a germ-free PBS control group taking intragastric administration; and the second group was a group of mice taking intragastric administration of a valine solution. The valine solution used and oral administration dosage were the same as those in Example 1.

TABLE 1

Effect of oral administration of amino acid solutions on the body weight of mice infected with H7N9 avian influenza virus

| | Weight percentage (%) | | | |
| --- | --- | --- | --- | --- |
| Number of days | PBS control group | Valine group | Isoleucine group | Lysine group |
| 0 | 100 | 100 | 100 | 100 |
| 1 | 101.723 ± 0.817 | 100.376 ± 1.297 | 99.507 ± 1.752 | 101.367 ± 1.395 |
| 2 | 101.406 ± 0.821 | 98.867 ± 1.562 | 101.437 ± 1.117 | 102.098 ± 2.162 |
| 3 | 101.908 ± 1.223 | 99.694 ± 0.997 | 99.198 ± 2.110 | 101.879 ± 1.964 |
| 4 | 100.119 ± 1.229 | 98.744 ± 1.464 | 98.165 ± 1.655 | 102.313 ± 1.689 |
| 5 | 98.535 ± 2.408 | 97.676 ± 1.212 | 97.327 ± 2.269 | 103.005 ± 2.212 |
| 6 | 93.258 ± 2.613 | 96.532 ± 2.247 | 93.634 ± 1.003 | 100.579 ± 1.842 |
| 7 | 87.671 ± 3.952 | 92.685 ± 3.532 | 87.056 ± 3.928 | 96.701 ± 2.301 |
| 8 | 83.740 ± 3.615 | 89.281 ± 4.239 | 82.431 ± 2.468 | 92.855 ± 2.717 |
| 9 | 84.558 ± 4.748 | 86.748 ± 5.032 | 81.257 ± 2.313 | 90.630 ± 2.539 |
| 10 | 89.634 ± 10.180 | 89.974 ± 7.480 | 80.011 ± 1.222 | 89.561 ± 4.417 |
| 11 | 99.606 | 95.825 ± 8.013 | — | 92.480 ± 7.016 |
| 12 | 101.574 | 100.740 ± 1.106 | — | 98.798 |
| 13 | 102.908 | 100.978 ± 0.863 | — | 101.100 |
| 14 | 102.664 | 101.789 ± 1.162 | — | 101.338 |
| 15 | 103.110 | 101.838 ± 0.276 | — | 101.960 |

Note:
"—" means all mice died and no body weight data; data without "±" means that there is only 1 mouse left, and the standard deviation is not calculated.

2. Effect of Oral Administration of Amino Acid Solutions on the Survival Rate of Mice Infected with H7N9 Avian Influenza Virus The statistical results of the survival of mice showed that compared with the PBS control group (with a survival rate of 10%), the group taking oral administration of valine can significantly improve the survival rate of mice infected with influenza virus, with a survival rate of 40%; the survival rate of the group taking oral administration of lysine after influenza virus infection was no different from that of the control group, both were 10%; however, the group taking The mice were given PBS or the valine solution every day. One week later, all mice were nasally infected with 1 LD50 H7N9 avian influenza virus. After challenge, they were given the PBS or the valine solution another 3 days. Lung samples were respectively taken by anatomy on day 0 and day 5 after influenza virus infection. The collected lung tissue samples were added with 1 ml of germ-free PBS (1 ml PBS/lung) and homogenized and broken by a homogenizer, and centrifuged to take the supernatant; the supernatant was frozen at −80° C. for detection of cytokine content and influenza virus content.

The cytokines tested included TNF-α, IL-1β, IFN-γ, and IFN-β. Among them, TNF-α, IL-1β, and IFN-γ were detected by Magnetic Luminex® Assay multiplex kit (R & D Systems), and IFN-β was detected by VeriKine Mouse IFN-β enzyme-linked immunosorbent assay kit (BioLegend).

Figure 3:
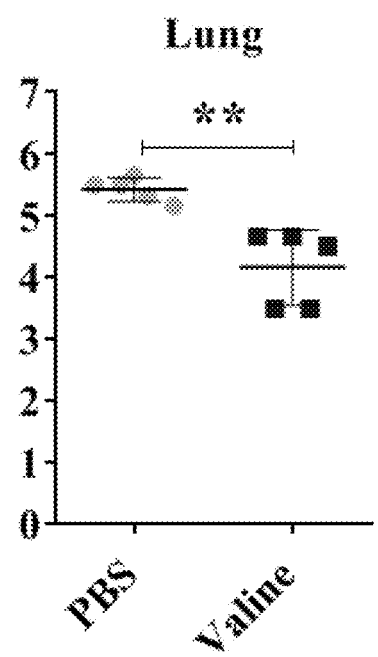
FIG. 3 is a schematic diagram showing the effect of oral administration of the valine solution on the virus content in the lungs of mice infected with H7N9 avian influenza virus, where the vertical axis shows the virus titer ($Log_{10}$ $EID_{50}$/ml).

1. Effect of Oral Administration of Valine on the Virus Content in the Lungs of Mice Infected with H7N9 Avian Influenza Virus After the mice were given valine and infected with H7N9 influenza virus, the proliferation of influenza virus in the lungs was determined. According to the results, FIG. 3 shows that oral administration of valine can significantly reduce the proliferation (P=0.0023) of influenza virus in the lungs after the infection. It shows that the oral administration of valine can resist influenza virus infection and has antiviral effect (Table 3, FIG. 3).

TABLE 3

Effect of oral administration of valine on the virus content in the lungs of mice infected with H7N9 avian influenza virus ($\log_{10}EID_{50}$/ml)

| Group | PBS control group | Valine group |
| --- | --- | --- |
| 5 days post infection | 5.434 ± 0.190 | 4.168 ± 0.614 |

Figure 4A:
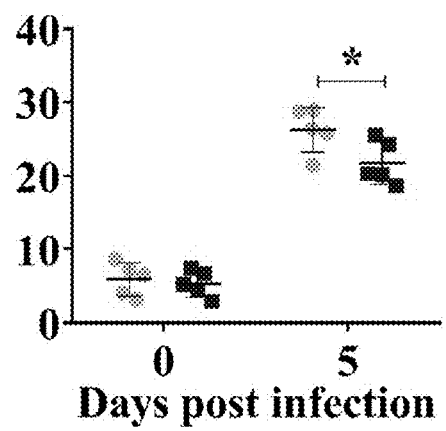
FIGS. 4A to 4D show the effect of oral administration of the valine solution on lung cytokines of mice infected with H7N9 avian influenza virus, where
Figure 4B:
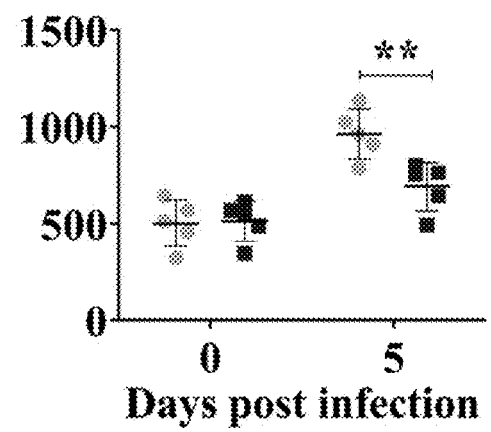
Figure 4C:
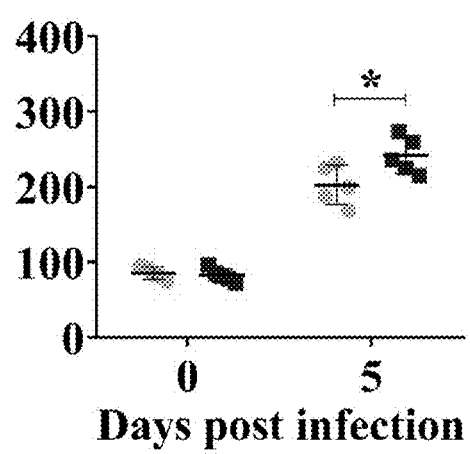
Figure 4D:
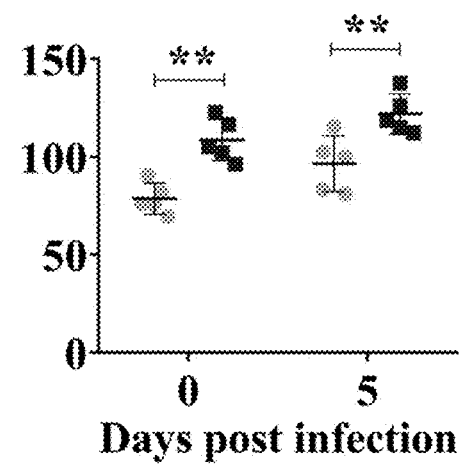

2. Effect of Oral Administration of Valine on the Cytokine Content in the Lungs of Mice Infected with H7N9 Avian Influenza Virus After oral administration of valine and infection with H7N9 influenza virus, the content of cytokines in lung tissue homogenate of mice on day 0 and day 5 post infection was determined. The results showed that on day 0 post infection, there were no differences in the levels of TNF-α, IL-1β and IFN-β (FIG. 4A, FIG. 4B, and FIG. 4C); the level of IFN-γ in the valine group was significantly higher than that in the control group (FIG. 4D); on day 5 post infection, the levels of TNF-α and IL-1β were significantly lower than that in the control group (FIG. 4A, FIG. 4B), and the levels of IFN-β and IFN-γ were significantly higher than that in the control group (FIG. 4C, FIG. 4D). The specific data is shown in Table 4.

The above results show that valine can improve the weight loss and mortality of mice infected with H7N9 infection, reduce the proliferation of influenza virus in lung tissue, and reduce inflammation by regulating the immune response to promote or inhibit the production of certain cytokines. The valine has higher antiviral effect.

TABLE 4

Effect of oral administration of valine on the content of lung cytokines of mice infected with H7N9 avian influenza virus (pg/ml)

| Group | | PBS control group | Valine group |
| --- | --- | --- | --- |
| Post infection 0 days | TNF-α | 5.900 ± 2.215 | 5.340 ± 1.787 |
| | IL-1β | 500.488 ± 121.592 | 512.836 ± 104.971 |
| | IFN-γ | 78.708 ± 7.851 | 108.583 ± 10.700 |
| | IFN-β | 85.508 ± 8.367 | 82.684 ± 8.872 |
| Post infection 5 days | TNF-α | 26.260 ± 2.992 | 21.820 ± 2.963 |
| | IL-1β | 962.762 ± 128.055 | 691.546 ± 125.531 |
| | IFN-γ | 96.462 ± 14.329 | 121.927 ± 10.241 |
| | IFN-β | 202.650 ± 26.095 | 241.686 ± 24.295 |

The valine is a newly discovered anti-influenza virus molecule, and valine is an essential amino acid in the animal body. It has the advantages of good safety, convenient and effective use, and can be used to develop a medicine to prevent or treat influenza virus infection, thus achieving broad application prospects.

What is claimed is:

1. A method for treating H7N9 avian influenza virus infection in a subject, comprising
   administering an effective amount of a composition to the subject in need of treatment for H7N9 avian influenza virus infection, wherein the composition consists of valine as the sole active ingredient in an aqueous solution at a concentration of 500 mg/mL, and
   causing a level of cytokine IFN-γ to increase in the subject.

2. The method of claim 1, wherein the composition is orally administered to the subject.

3. The method of claim 1, wherein the composition is administered to the subject for at least 7 days.

* * * * *